(12) United States Patent
Treillet et al.

(10) Patent No.: US 6,444,987 B1
(45) Date of Patent: Sep. 3, 2002

(54) GAMMA CAMERA USABLE IN TWO POSITIONS OF A PATIENT

(75) Inventors: Jean Treillet, Samary sur Mer; Christian Pare, Plaisir, both of (FR)

(73) Assignee: Sopha Medical Vision International, Paris (FR)

( * ) Notice: Subject to any disclaimer, the term of this patent is extended or adjusted under 35 U.S.C. 154(b) by 0 days.

(21) Appl. No.: 09/449,792

(22) Filed: Nov. 26, 1999

(30) Foreign Application Priority Data

Nov. 27, 1998 (FR) .............................. 98 15000

(51) Int. Cl.[7] .................. G01T 1/20; G01T 1/166; G01T 1/164
(52) U.S. Cl. .................. 250/363.05; 250/363.01; 250/363.08
(58) Field of Search .................. 250/363.01, 363, 250/363.08

(56) References Cited

U.S. PATENT DOCUMENTS

| 4,774,411 A | * | 9/1988 | Span | 250/363.05 |
|---|---|---|---|---|
| 5,105,086 A | * | 4/1992 | Pierfitte et al. | 250/363.08 |
| 6,204,503 B1 | * | 3/2001 | Pierfitte et al. | 250/363.05 |
| 6,255,656 B1 | * | 7/2001 | Stark | 250/363.08 |
| H12 H | * | 1/1986 | Bennett et al. | 250/363.05 |

FOREIGN PATENT DOCUMENTS

| FR | 0 517 600 | 9/1992 |
| WO | WO96 30781 | 10/1996 |

\* cited by examiner

Primary Examiner—Georgia Epps
Assistant Examiner—Alicia M Harrington
(74) Attorney, Agent, or Firm—Nilles & Nilles, S.C.

(57) ABSTRACT

A gamma camera is made with two rings, each ring bearing a detector. A flap of a support of the detector can be unfolded or folded against a front face of the machine. In the folded position, the machine can be used to carry out tomography scans or standard whole-body examinations. In the unfolded position, the flap enables the performance of whole-body examinations on a bed-ridden patient who remains in his hospital bed.

7 Claims, 2 Drawing Sheets

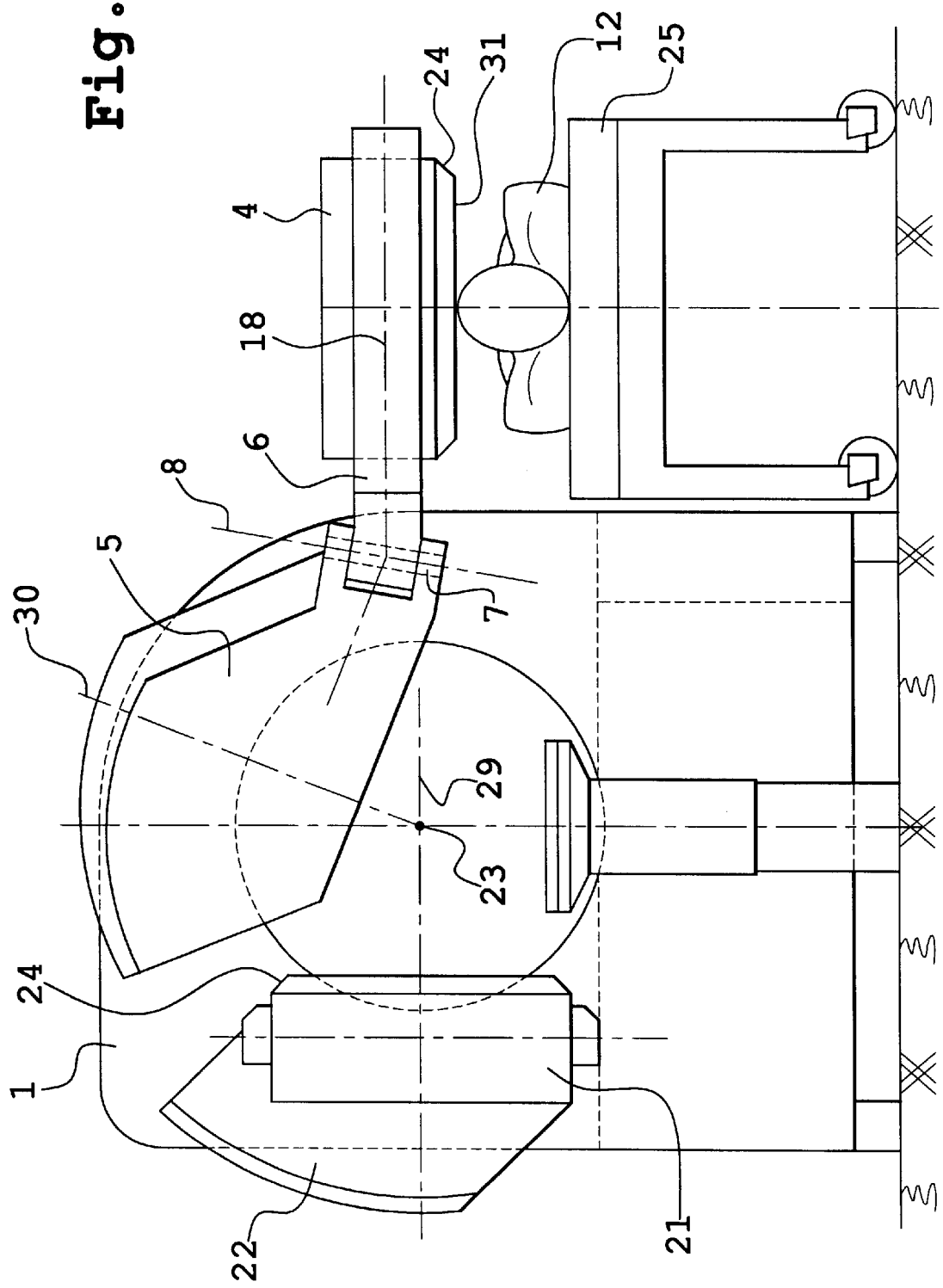

GAMMA CAMERA USABLE IN TWO POSITIONS OF A PATIENT

BACKGROUND OF THE INVENTION

1. Field of the Invention

An object of the present invention is a universal-purpose, tunnel type convertible gamma camera preferably with two rings. The aim of the invention is to make the design of such a gamma camera more rational so that it can be used for a plurality of purposes.

Gamma cameras of the PET and SPECT (positron emission tomography, and single-photon emission computer tomography) are known in the field of nuclear medicine. In the former case, they have to detect the appearance of phenomena of nuclear emission in coincidence on two opposite and facing detectors. In the latter case, they are used to detect nuclear emissions sent in at least one direction. The invention can be applied to either of these two techniques.

The principle of these phenomena is as follows. A radiological marker is injected into a body to be examined, for example a patient's body. This marker is more generally technetium, and sometimes thallium, or another marker. Depending on a metabolic charge, the markers will get fixed preferably in certain organs of a patient's body. Through the density of this fixation, they reveal the functional state of the organ in which they get fixed. These markers emit camera rays during their metabolization. These gamma rays are detected by a detector.

A detector of this kind has a collimator on an input face. The role of this collimator is to acquire an image in projection. However, there are known ways of having collimators with inclined holes or focused holes. The gamma rays that cross the collimator then reach a scintillator whose role is to convert each gamma ray into a light scintillation. This light scintillation is detectable by a set of photomultiplier tubes placed downline from the scintillator. The photomultiplier tubes detect the scintillations and deliver corresponding electrical signals whose amplitude and shape reveal the nature and position of the nuclear event detected. These signals are processed, especially in barycenter-determining matrices, to constitute an image revealing this nuclear activity.

2. Description of the Related Art

Several types of examinations are performed. There are especially, on the one hand, tomography operations and, on the other hand, whole-body images. In one tomography operation, a projected image is acquired for a given incidence of the detector with respect to the patient's body. Then another projected image is acquired for another incidence, offset by some degrees with respect to the former. Continuing progressively in this way, a great many projected images are acquired. From these images, through the use of image reconstruction algorithms (of the same type as those used in tomodensitometry) a 3D image is acquired of the organ being studied. The projected images are acquired slowly. Typically, the period of acquisition of a projected image oscillates between 5 seconds for the fastest ones, up to 2 minutes for the finer images. In the European patent application EP-A-0 517 600, it has been explained that, to accelerate image acquisition in tomography, it is preferable to use two detectors, and also to place these detectors at 90° to each other around the patient's body.

Another examination relates to so-called whole-body images. To acquire an image of this kind, the detector is moved in translation along the patient's body while he or she is supine. This type of examination is used to take essentially an angiographic image of the patient's legs, especially to detect problems of vascular insufficiency. Preferably, also in this case, to increase image quality, a second detector is placed beneath the patient's body. The patient then gets translated between these two detectors. With certain machines, the patient is immobile and the machine moves with respect to him or her.

Other examinations are practiced such as cardiography with exertion. For these other examinations, the patient is subjected to physical exertion at the same time as the images are taken.

The different types of images made require that the detectors should be highly mobile with respect to one another. The machines designed to carry them out efficiently are machines of two types: tunnel machines or open-gantry machines, that is machines with arms. In a tunnel machine, the patient goes into a tunnel whose walls mechanically support the detectors. In a machine with arms, a gantry holds two arms each supporting a detector, the patient being presented between these arms. There is the known exemplary patent application PCT/US95/13180 in which there is a combined machine with both a tunnel and arms. The problem presented by these different machines is that they are complicated to manufacture. Indeed, the detection technology, especially that of collimators, requires heavy detectors. In practice, the weight of these detectors may be in the range of 300 or 400 kilos. Given the different ways of positioning these detectors around the patient's body and the required precision of about 1 millimeter each time, the gantries that bear these machines are massive. They are all the more massive as, in the hospitals and medical centers in which they are installed, the floor on which they rest is often not perfect. In these cases, these gantries must be capable of coping with these problems of the floor.

Besides, to go from a tomography type of examination to a whole-body type of examination, the tunnel machines and the machines with arms have different advantages and drawbacks. In the tunnel machine, it is enough to make the patient's bed go through the tunnel. In a machine with arms, the bed that supports the patient must be rotated by 90° with respect to the machine before the whole-body examination can be made. This drawback however is compensated for with this machine in that it enables the use of the patient's hospital bed instead of the examination bed. For patients who are bed-ridden or cannot be carried out of their beds, it is enough to replace the bed of the machine with the patient's bed.

For various reasons, however, tunnel machines are preferred.

One problem to be resolved therefore is that of designing a tunnel machine that can be used to perform angiography on patients when these patients are left in their hospital bed and when they are not lying on the examination bed. This problem is partially resolved by the combined machine referred to here above. However, it is costly to design since it includes all the mechanisms of the two machines. Furthermore, for examinations during which the patient is sitting or facing the machine, or else doing a work-out in an exertion machine, the frontal presentation of the detectors proposed by this machine makes these examinations impractical to perform. The space taken up by the underframe of this combined machine as well as the presence of the patient's own bed are a hindrance to these examinations.

OBJECTS AND SUMMARY OF THE INVENTION

In the invention, this problem is resolved by choosing a tunnel machine. This tunnel machine however is not a complicated one. The problem of complexity is resolved therein by fitting out a support of a detector with a folding arm. The folding arm or flap can thus take two preferred positions. A first position of the flap in this support presents the detector so that it faces the tunnel of the machine. In this position, it is possible to carry out both tomography and whole-body examinations. These whole-body examinations are then made on patients likely to get placed in the machine bed. In the other position, a single detector is transferred by the folding arm. It is transferred to the side of the machine. Then, parallel to this tunnel of the machine, there is far more space available to place an examination chair, an exertion machine or a bed for a patient who cannot be transferred.

In this case, in the invention, these examinations will be made with only one detector. Therefore, to obtain adequate image quality, the shooting time for each image must be sufficiently long. However, this does not entail any penalties since these examinations are relatively infrequent and, from this point of view, the invention achieves an efficient compromise between the cost of the machine and its real efficiency. Furthermore, the system of folding the arm is very simple. Consequently, it does not give rise to any major additional cost.

An object of the invention therefore is a tunnel type gamma camera with at least one ring rotating about an axis of rotation passing into a tunnel, this ring bearing a detector by means of a support, wherein the support has a folding arm mechanically linked firstly to the ring and secondly to the detector, this arm being provided with a hinge with an axis offset with respect to the detector and being capable of occupying at least two angular positions with respect to this offset axis, a first angular position enabling the detector that it carries to be presented so that it faces the tunnel, and a second angular position enabling it to be presented beside the tunnel.

BRIEF DESCRIPTION OF THE DRAWINGS

The invention will be understood more clearly from the following description and the accompanying figures. These figures are given purely by way of an indication and in no way restrict the scope of the invention. Of these figures:

FIG. 3 shows a view of a use of the machine of the invention as well as particular features of the making of the hinge of the folding arm.

DESCRIPTION OF THE PREFERRED EMBODIMENTS

Figures 1, 2A, 2B, 2C:
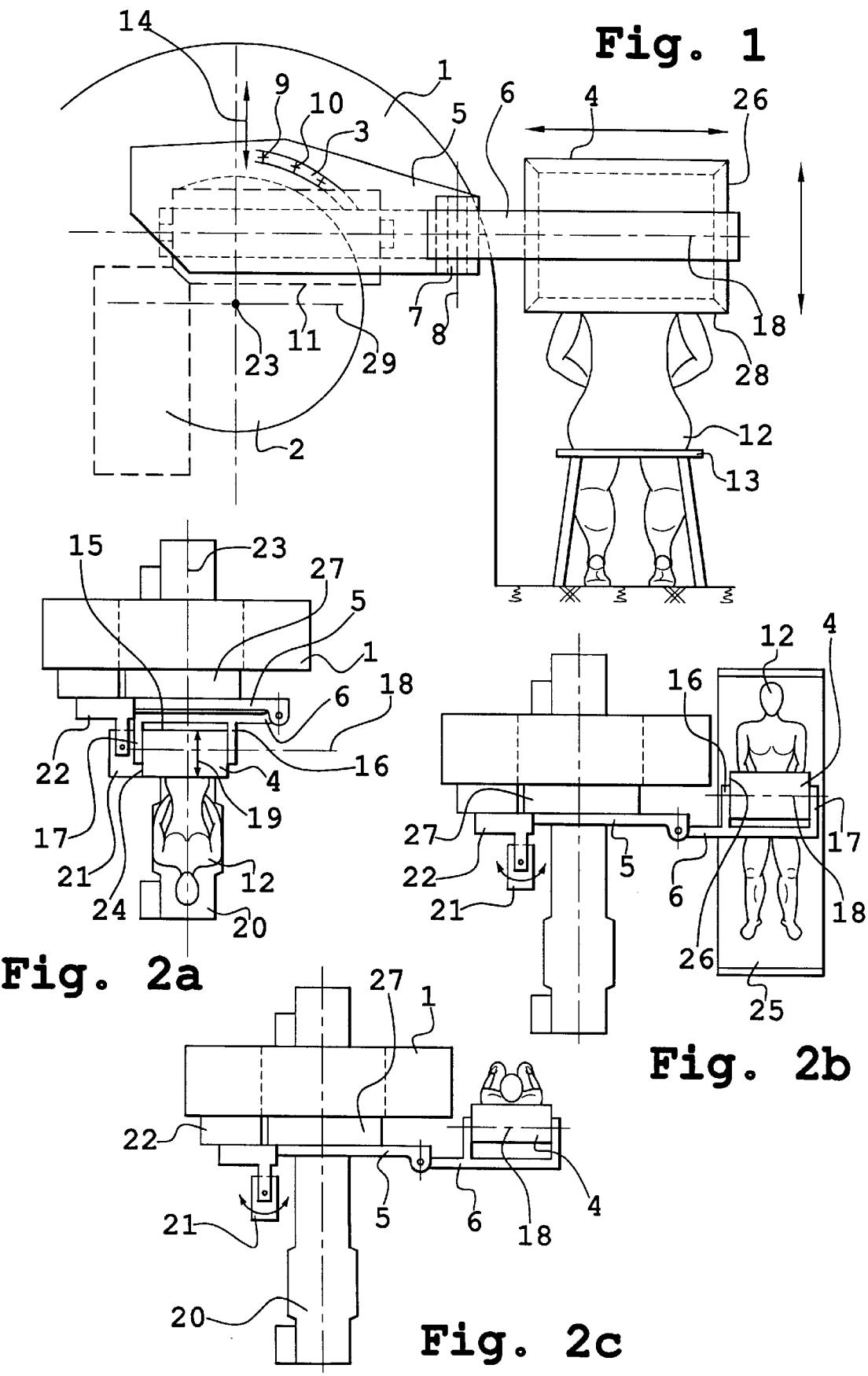
FIG. 1 shows a view of a gamma camera according to the invention with a folding arm that is in a position such that the detector is located beside the examination tunnel of the machine.
FIGS. 2a to 2c show different possibilities of use of the machine of the invention according to the types of examinations made.

FIG. 1 shows a gamma camera according to the invention. This gamma camera has a frame 1 that has a tunnel going through it, the frame rotationally supporting a ring 3. In practice, the frame 1 supports two rings. Each ring has a detector. The ring 3 thus carries a detector 4 by means of a support 5. The support 5 has the shape of a flat vertical plate. It will be seen further below that this support is itself capable of being mobilized in vertical and horizontal translation in a plane that is vertical to the ring 3. The support 5 of the invention has the essential particular feature of having a flap 6. The flap 6 or folding arm is fixed to the plate 5 by means of a hinge 7 enabling the folding of the flap 6 about an axis 8.

In a first angular position, the flap 6 is folded down on the plate 5 brought to the ring 3. When the flap 6 occupies the first angular position, the detector 4 indicated by the contour in dashes 11 is facing the tunnel 2 of the machine 1. In the second angular position, the detector 4 is presented beside the tunnel. This is obtained by the fact that the axis 8 is offset laterally with respect to the detector 4. The fastening of the plate 5 to the ring 3 is shown schematically with screws 9 and 10. In practice, one or more other plates are mechanically linked to the ring 3, the plate 5 being movable with respect to this or these other plates. In practice, a translation mechanism is made between the ring 3 and the plate 5, enabling the plate 5 to shift in a plane parallel to the entry face of the machine 1. This shift has lateral, vertical and combined translational motions.

In the type of examination shown, a patient 12 is seated on a seat 13 with his back and shoulders before a detection face (invisible herein) of the detector 4. It will be observed that the fact of placing the detector, with the flap 6, beside the frame 1 makes it possible to have a large amount of space to place the seat 13 or an exertion machine therein. By using the vertical translation 14 which puts the plate 5 into motion, an equivalent shift of the detector is prompted along the back of the patient 12. If necessary, the patient could be oriented with his belly placed flat against the detection face of the detector 4.

The passage from one angular position of the flap 6 to the other position is very easy. It is enough to place the axis 8 vertically. In this case, the flap 6 can be rotated by hand after it has been unlocked from the plate 5 so that it takes the position shown. The two positions are stable. Locking mechanisms are designed to hold the flap in each of the positions.

FIGS. 2a to 2c show particular features of use of a double ring machine. FIG. 2a shows the plate 5 and the flap 6, where the latter takes up a first position in which it is placed flat against the plate 5. The flap 6 has a bracket 15 provided with two legs, 16 and 17 respectively. Bearings not shown but fixed to the legs 16 and 17, at their ends, enable the detector 4 to be kept in orientation about an axis (in this case a horizontal axis) 18. A small dimension 19 of the detector 4 can easily be contained in the depth of the bracket 15. The detector 4 has a rather elongated and rectangular shape. The axis 18 goes through half the small side 19. A large dimension of the detector 4 is housed between the legs 16 and 17 of the bracket 15. In this way, this bracket 15 can make the detector 4 undergo a 90° rotation with respect to the horizontal position shown.

In FIG. 2a, a patient 12 is lying on an examination bed 20 of the machine. Therein, he can undergo a whole-body examination or a tomography scan. For the latter, preferably a second detector 21 is used, borne by a second support 22 and presenting the patient at 90° of the presentation of the detector 4. To acquire the tomography, the plate 5 and the support 22 rotate together in the frame 1 along a rotational axis 23 passing to the center of the tunnel 2 of the machine. The axis 18 is orthogonal to the axis 23 in both angular positions of the detector 4. By their shifts in translation (vertical and horizontal), the supports 5 and 22 can be made to approach each other so that a ridge 24 common to the two detectors 4 and 21 come into a contact. For an angiography examination or more generally for a whole-body type of examination, it is enough to make the support 22 rotate alone around the body of the patient 12 so that he gets placed beneath the bed 20. It is then possible to acquire an 10 image of this kind with two detectors simultaneously which improves their quality. In these two examinations, the bed 20 can slide with respect to the frame 1 along the tunnel 2.

In FIG. 2b, the flap 6 takes the second position. The legs 16 and 17 of the brackets, which are substantially horizontal, are presented above the body of the patient 12 who is lying on his or her hospital bed 25 and not on an examination bed. As in FIG. 2a, the active face of the detector 4 remains facing downwards. As compared with FIG. 1, it can be seen that, from one figure to another, the detector 4 has tilted around the axis 18 so as to show its small side 26 vertically or horizontally as the case may be. FIG. 2c shows a top view of the examination situation of FIG. 1.

The mechanisms of vertical and horizontal translation are positioned in a space 27 located between the frame 1 (and therefore the rings 3) and supports 5 an 22. They are of a known type and consist of a system of rails and slides; In one practical embodiment, three parallel plates are used to obtain these motions.

FIG. 3 gives a view, in a front face of the machine, of a particular embodiment of the link 7 between the flap 6 and the plate 5. Indeed, as can be seen in FIG. 1, the heightwise position of the detector 4 may prove to be inappropriate. Especially, in the depiction, the support 5 is in the top position with respect to the frame 1 owing to the rotation of the ring 3, when the flap 6 is shifted to take the second position. Normally, the plate 5 has a path of travel in vertical elevation that is limited. The limit is such that the lower edge 28 of the detector 4 comes only slightly above a horizontal plane 29 going through the rotational axis 23.

It is also possible to use the low position of the support 5. To this end, the flap 6 is closed on the support 5. It is locked and the ring 3 is made to rotate by 180°. Then, the flap 6 is open again. In this case, the useful space for the examination must be made to the left of the tunnel instead of being made to the right as in this case. However, a comparable situation is obtained: the edge 28 which will then be the upper edge of the detector 4 in this case will only come slightly above the horizontal plane 29.

A problem therefore arises if the zone of examination in the body 12 of the patient is located precisely around the horizontal plane 29. To resolve this problem, it is possible to provide a higher or lower seat 13. This is also possible for an exertion machine. On the contrary, for a hospital bed, it is not really possible because these beds do not make it possible, for simple beds, to obtain a great range of play in height. To this end, a different procedure will be used in accordance with FIG. 3.

In this FIG. 3, the ring 3 no longer occupies a rotational position corresponding to the horizontal presentation of the detectors of the previous figures. On the contrary, the ring 3 will have rotated by a few degrees. In one example, it will have rotated by 24° and will take a direction 30. The direction 30 is a direction contained in a plane passing through the axis 23 and perpendicular to the detection face of the detector 4 when it occupies the first position (that of FIG. 2a). The direction 30 is therefore inclined by 24° with respect to the vertical. The axis 8 of the hinge 7 in this embodiment is then not orthogonal to the axis 18. On the contrary it is inclined by 12°, half of the tilt of the direction 30, with respect to the axis 18. The axis 18 is thus inclined with respect to a plane perpendicular to a detection face of the detector 4. It is not parallel to a plane of this kind. Furthermore, the flap 6 is mounted in the hinge 7, in being itself inclined by an angle equal to 12°. In other words, when the flap 6 is unfolded, it forms an angle of about 156° with respect to its orientation when it is folded down. Owing to the inclination of the direction 30 and the lateral shift of the hinge 7 of the plate 5, this hinge 7 gets placed at a lower level. This fact of being placed at a lower level then makes it possible to cross the altitude of the horizontal 29 towards downwards so that, in the unfolded position, the detector 4 can be brought sufficiently low, near the body 12 of a patient lying on his hospital bed 25. The values of 12° and 24° are preferred solutions of the invention. However it is possible to obtain a situation where a tilt of this kind is not equal to 12° (and 24°) but only in the range of 12° (and 24°), for example between 90 and 15° (and 18° and 24°).

In view of the weight of the detector 4, which is about 400 kilos, it cannot be envisaged that this detector 4, in its horizontal position, will be shifted by hand. In this case, the following procedure is used. While the flap 6 is folded down on the plate 5, a rotation of the ring 3 is used to bring the axis 8 into a vertical position. In this case, the axis 8 is placed at the top of the machine. Then, the locking of the flap 6 on the plate 5 is released. Then, the flap 6 is rotated by hand or with a slight motor drive. When the flap 6 takes up the unfolded position, it is locked in this position and the rotation of the ring 3 is completed to bring the detector 4 to the horizontal position. In this case, the ring 3 undergoes two 12° rotations, a first rotation to orient the axis 8 vertically and the second one to place the detector 4 horizontally.

We claim:

1. Tunnel type gamma camera with at least one ring rotating about an axis of rotation passing into a tunnel, this ring bearing a detector by means of a support, characterized in that this support has a flap mechanically linked firstly to the ring and secondly to the detector, this flap being provided with a hinge with an axis offset with respect to the detector and being capable of occupying at least two angular positions with respect to this offset axis, a first angular position enabling the detector that it carries to be presented so that it faces the tunnel, and a second angular position enabling it to be presented beside the tunnel.

2. Gamma camera according to claim 1, characterized in that the offset axis is inclined with respect to a plane perpendicular to a detection face of the detector.

3. Gamma camera according to claim 2, characterized in that the inclination is equal to an angle of about 12°.

4. Gamma camera according to claim 1, characterized in that the detector has an axis of orientation orthogonal to the axis of rotation.

5. Gamma camera according to claim 4, characterized in that the axis of orientation is parallel to a large side of the detection face of the detector.

6. Gamma camera according to claim 4, characterized in that the support has a bracket with a depth greater than half of a small side of the detection face of the detector.

7. Gamma camera according to claim 1, characterized in that the support comprises a plate.

* * * * *